United States Patent [19]

Saville

[11] Patent Number: Plant 5,483

[45] Date of Patent: Jun. 4, 1985

[54] ROSE PLANT

[75] Inventor: F. Harmon Saville, Rowley, Mass.

[73] Assignee: Nor'East Miniature Roses, Inc., Rowley, Mass.

[21] Appl. No.: 556,266

[22] Filed: Nov. 30, 1983

[51] Int. Cl.[3] ..... A01H 5/00

[52] U.S. Cl. ..... Plt./10

[58] Field of Search ..... Plt./10

*Primary Examiner*—Robert E. Bagwill

*Attorney, Agent, or Firm*—Vincent G. Gioia

[57] ABSTRACT

A new miniature rose variety of bright orange red coloring.

1 Drawing Figure

The present invention relates to a new and distinct variety of rose plant of the miniature rose class, which was originated by my crossing as seed parent the rose known as "Sheri Anne" (U.S. Plant Pat. No. 3,826) and an unnamed, unpatented seedling of my creation as pollen parent. The varietal denomination of this new variety is "Savabrez".

Among the novel characteristics possessed by this new variety which distinguish it from its parents and all other varieties of which I am aware are its capsicum red buds which open into bright orange red flowers quickly and display irregular yellow coloring at the flower centers. Asexual reproduction by budding of the new variety as performed in Essex County, Mass., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "33A" is plate 33A of The Royal Horticultural Society Colour Chart.

Parentage: Seedling.

*Seed parent.*—"Sheri Anne".

*Pollen parent.*—Unnamed seedling.

Class: Miniature.

The following observations are made of specimens grown outdoors in Essex County, Mass., during the month of October.

FLOWER

Blooming habit: Recurrent.

Bud:

(1) *Size.*—Medium.

(2) Form.—Short pointed.

(3) *Color.*—When sepals first divide — capsicum red near 33A. When petals begin to unfurl — color of petal undersurface appears lighter toned approaching shrimp red 33D.

(4) *Sepals.*—Length same as bud, slightly foliated.

(5) *Peduncle.*—Length — $\frac{3}{4}$ to 1 inch. Aspect — straight. Strength — erect. Color — near 138C.

Bloom:

(1) *Size.*—Average size when fully expanded — about 1 to $1\frac{1}{4}$ inches.

(2) *Borne.*—Primarily several together in sprays.

(3) *Form.*—High centered at first, becoming flat, petals reflex upon opening but often appear loose.

(4) *Petalage.*—Number of petals under normal conditions — about 16 to 20.

(5) *Color.*—Capsicum red buds unfurl into orange red flowers with predominant coloring in the range of 34A through 33A. Petal undersurface tends to lighter tonality 34C through 33D. Flowers open quickly revealing yellow lower segments of inner petals near 17D. The yellow-red line of demarcation appears more sharply defined on some petal top surfaces than on others but the yellow coloring is not clearly visible until flowers are fully open and then is limited to the immediate vicinity of the flower center.

Petals:

(1) *Texture.*—Thick.

(2) *Appearance.*—Inside — satiny, outside — satiny.

(3) *Form.*—Oval.

(4) *Arrangement.*—Regularly arranged, shingle-like.

(5) *Petaloids in center.*—Few.

(6) *Persistence.*—Drop off cleanly.

(7) *Fragrance.*—Slight.

(8) *Lasting quality.*—Long lasting on plant and as cut flower.

REPRODUCTIVE ORGANS

Stamens, filaments and anthers:

(1) *Arrangement.*—Regularly arranged around styles.

(2) *Color.*—Near 24B.

Pollen:

*Color.*—Near 26A.

Styles: Even, medium length.

Stigmas:

*Color.*—Near 157A.

Hips:

*Shape.*—Globular.

*Size.*—Medium.

*Color.*—Orange red.

*Do seeds protrude'*—Sometimes.

PLANT

Form: Upright.

Growth: Vigorous.

*Height attained.*—About 12 to 18 inches.

Foliage: Compound 5 to 7 leaflets.

(1) Size.—Medium.

(2) *Quantity.*—Abundant.

(3) *Color.*—New foliage: Upper side — near to 141B. Under side — near to 148C. Old foliage: Upper side — near 139A. Under side — near 148B.

(4) *Shape.*—Oval.

(5) *Texture.*—Upper side is semi-glossy and under side is matte.

(6) *Edge.*—Serrated.

(7) *Serration.*—Serrulate.

(8) *Leaf stem.*—Color — near to 184A. Under side — near 199C.

(9) *Stipules.*—Medium.

(10) *Resistance to disease.*—Blackspot — average. Mildew — average. Rust — average.

Wood:

(1) *New wood.*—Color — near 146C. Bark — smooth.

(2) *Old wood.*—Color — near 152A. Bark — smooth.

Thorns:

(1) *Thorns.*—Quantity (main stalk): ordinary. On laterals from stalk — few. Form — Long, pointed, curving downward. Length — medium. Color — near 187D. Position — irregular.

(2) *Prickles.*—None.

Winter hardiness: Requires ordinary protection in extreme climates.

I claim:

1. A new and distinct variety of rose plant of the miniature rose class, substantially as shown and described, characterized particularly by capsicum red buds which open quickly into bright orange red flowers with irregular yellow flower centers in the fully open stage.

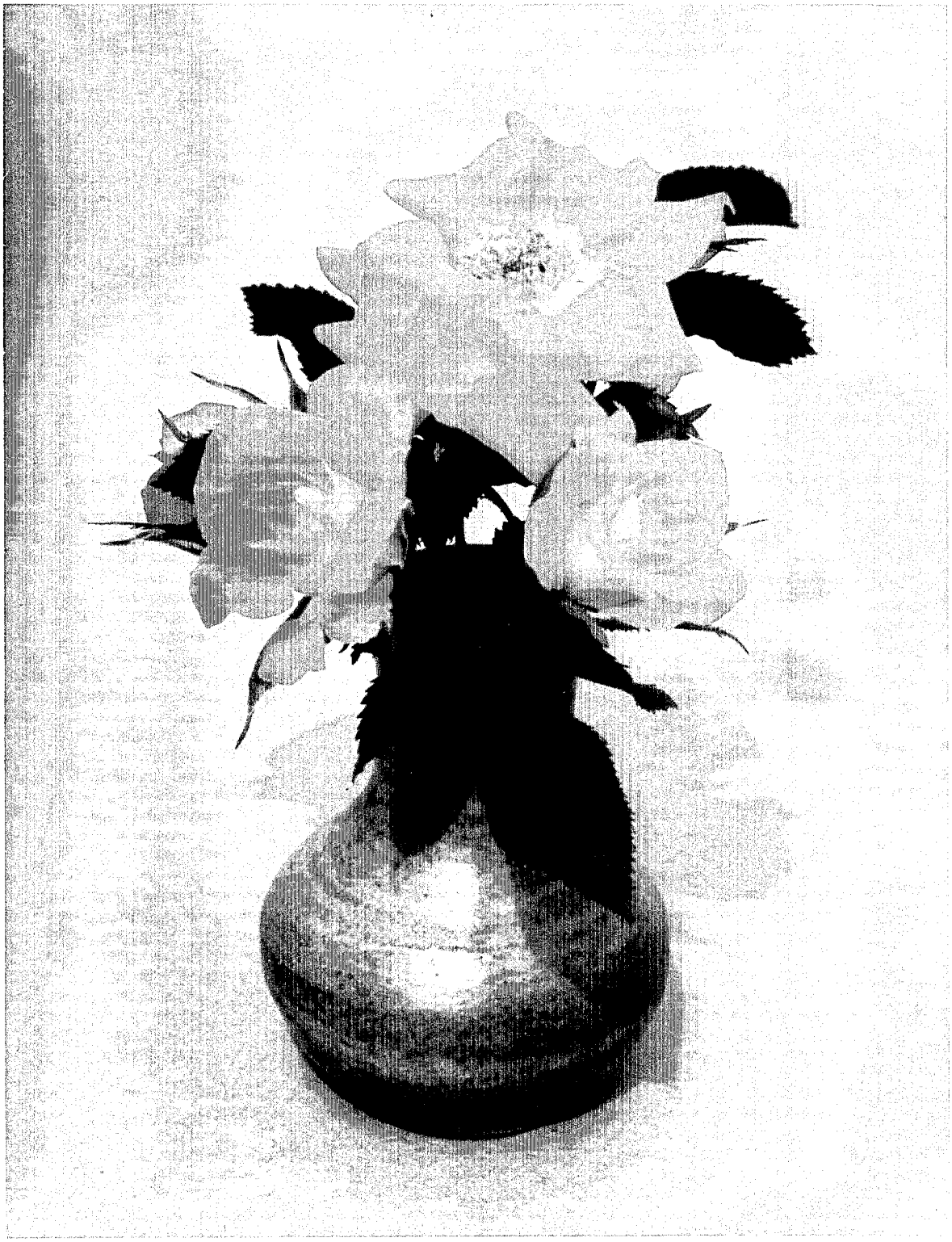

* * * * *